United States Patent [19]

Lewis et al.

[11] Patent Number: 5,140,989

[45] Date of Patent: * Aug. 25, 1992

[54] EXAMINATION INSTRUMENT FOR OPTICAL-RESPONSE DIAGNOSTIC APPARATUS

[75] Inventors: Gary D. Lewis, St. Clair Shores, Mich.; Hugh F. Stoddart, Groton, Mass.

[73] Assignee: Somanetics Corporation, Troy, Mich.

[*] Notice: The portion of the term of this patent subsequent to Feb. 18, 2003 has been disclaimed.

[21] Appl. No.: 827,526

[22] Filed: Feb. 10, 1986

Related U.S. Application Data

[63] Continuation-in-part of Ser. No. 542,022, Oct. 14, 1983, Pat. No. 4,570,638.

[51] Int. Cl.⁵ ............................................. A61B 6/00
[52] U.S. Cl. .................................... 128/665; 128/666
[58] Field of Search ............................ 128/632-633, 128/653, 664-666

[56] References Cited

U.S. PATENT DOCUMENTS

| | | | |
|---|---|---|---|
| 738,707 | 9/1903 | VanNort | 362/280 |
| 2,358,992 | 9/1944 | Millikan | 356/41 |
| 2,414,747 | 1/1947 | Kirschbaum | 128/204.23 |
| 2,423,855 | 7/1947 | Smaller | 356/41 |
| 2,437,916 | 3/1948 | Greenwald | 128/665 |
| 2,439,857 | 4/1948 | Millikan | 356/41 |
| 2,442,462 | 6/1948 | Kirschbaum | 128/633 |
| 2,475,132 | 7/1949 | Ergen | 318/678 |
| 2,640,389 | 6/1953 | Liston | 128/633 |
| 2,685,815 | 8/1954 | Mayne | 128/633 |
| 2,706,927 | 4/1955 | Wood | 356/41 |
| 2,760,485 | 8/1956 | Adelman | 128/633 |
| 2,790,438 | 4/1957 | Taplin et al. | 128/633 |
| 3,036,568 | 5/1962 | Stark | 128/664 |
| 3,123,066 | 3/1964 | Brumley | 128/634 |
| 3,136,310 | 6/1964 | Meltzer | 128/634 |
| 3,152,587 | 10/1964 | Ullrich et al. | 128/633 |
| 3,280,636 | 10/1966 | Tomberg | 73/432 |
| 3,313,290 | 4/1967 | Chance et al. | 128/633 |
| 3,335,716 | 8/1967 | Alt et al. | 128/664 |
| 3,349,762 | 10/1967 | Kapany | 128/666 |
| 3,406,681 | 10/1968 | Zandman | 128/645 |
| 3,412,729 | 11/1968 | Smith, Jr. | 128/633 |
| 3,461,856 | 8/1969 | Polanyi | 128/633 |
| 3,511,227 | 5/1970 | Johnson | 128/666 |

(List continued on next page.)

FOREIGN PATENT DOCUMENTS

| | | | |
|---|---|---|---|
| 484366 | 7/1975 | Australia | 128/633 |
| 3015 | 7/1979 | European Pat. Off. | 356/41 |

(List continued on next page.)

OTHER PUBLICATIONS

IBM Technical Disclosure Bulletin, vol. 10 No. 3, Aug., 1967 "Stacker Selection System" by A. K. Brooks & C. J. Kellerman, pp. 225-226.

(List continued on next page.)

Primary Examiner—William E. Kamm
Assistant Examiner—J. P. Wacyk
Attorney, Agent, or Firm—Price, Heneveld, Cooper, De Witt and Litton

[57] ABSTRACT

An examination instrument for optical apparatus, including a pair of optical heads mounted for relative movement toward and away from one another upon an elongated support, and having means (e.g., an electrical transducer) for producing an electrical signal which is specifically representative of the distance between the optical heads at various positions of relative movement therebetween, for use in analyzing test data obtained by the optical heads. The instrument also includes a test sequence actuation switch disposed in a position where the operator may readily initiate a test sequence without changing his grip upon the instrument as it is held in place on the test subject. The optical heads are mounted on stand-off members which position the heads in spaced relation alongside the elongated support and at an angle relative to one another, to facilitate use on the human breast. The optical heads include internal light-guides for emitting and/or receiving light, and such light-guides are preferably matched optically to electro-optical detectors carried by the optical heads, for optimum performance.

56 Claims, 3 Drawing Sheets

U.S. PATENT DOCUMENTS

| | | |
|---|---|---|
| 3,517,999 | 6/1970 | Weaver ................................ 356/32 |
| 3,527,932 | 9/1970 | Thomas ................................ 128/23 |
| 3,602,213 | 8/1971 | Howell et al. ................. 128/2.05 P |
| 3,628,525 | 12/1971 | Polanyi et al. ................. 128/2.05 P |
| 3,672,352 | 6/1972 | Summers ........................... 128/2 R |
| 3,674,013 | 7/1972 | Polanyi ........................... 128/2.05 D |
| 3,677,648 | 7/1972 | Dorsch ................................ 356/40 |
| 3,690,769 | 9/1972 | Mori ................................... 356/41 |
| 3,704,706 | 12/1972 | Herczfeld et al. . |
| 3,709,612 | 1/1973 | Clemens ........................ 128/633 X |
| 3,710,011 | 1/1973 | Altemus et al. ................. 128/5.4 R |
| 3,734,091 | 5/1973 | Taplin ............................... 128/142 |
| 3,748,471 | 7/1973 | Ross et al. ........................ 250/333 |
| 3,769,963 | 11/1973 | Goldman et al. ................. 128/2 R |
| 3,769,974 | 11/1973 | Smart et al. ....................... 128/633 |
| 3,777,738 | 12/1973 | Sugita et al. ....................... 128/2 T |
| 3,787,119 | 1/1974 | Rybak ................................ 356/73 |
| 3,810,460 | 5/1974 | Van Nie ............................. 128/666 |
| 3,814,081 | 6/1974 | Mori ................................... 128/2 L |
| 3,822,695 | 7/1974 | Takayama .......................... 128/2 L |

(List continued on next page.)

FOREIGN PATENT DOCUMENTS

| | | |
|---|---|---|
| 19478 | 11/1980 | European Pat. Off. ............ 318/678 |
| 23186 | 1/1981 | European Pat. Off. ............. 356/41 |
| 46601 | 3/1982 | European Pat. Off. ............ 128/645 |
| 2023318 | 12/1971 | Fed. Rep. of Germany ...... 128/633 |
| 2053301 | 5/1972 | Fed. Rep. of Germany ...... 128/633 |
| 2263890 | 7/1973 | Fed. Rep. of Germany ..... 128/2.05 D |
| 2065515 | 3/1974 | Fed. Rep. of Germany ..... 128/2 R |
| 2538985 | 5/1976 | Fed. Rep. of Germany ........ 356/41 |
| 2517129 | 6/1976 | Fed. Rep. of Germany ........ 356/32 |
| 2641144 | 3/1977 | Fed. Rep. of Germany ........ 356/41 |
| 2741913 | 4/1978 | Fed. Rep. of Germany ...... 128/2 T |
| 2741981 | 4/1978 | Fed. Rep. of Germany ...... 250/333 |
| 2724543 | 12/1978 | Fed. Rep. of Germany ..... 128/2.05 V |
| 2726606 | 12/1978 | Fed. Rep. of Germany ...... 128/2 L |
| 2827488 | 2/1979 | Fed. Rep. of Germany ...... 128/2 T |
| 2823769 | 12/1979 | Fed. Rep. of Germany ...... 250/343 |
| 2947194 | 7/1981 | Fed. Rep. of Germany ..... 128/2 R |
| 2481917 | 11/1981 | France ................................ 128/664 |
| 2517953 | 6/1983 | France ................................ 128/634 |
| 149157 | 7/1981 | German Democratic Rep. .................................. 128/633 |

(List continued on next page.)

OTHER PUBLICATIONS

IBM Technical Disclosure Bulletin, vol. 10, No. 3, Aug., 1967 "Micr Automatic Gain Control" by R. W. Arnold, pp. 227–228.

"Biomedizinische Technik" (Germany) Band 17 1972 No. 3, p. 93.

"Biomedizinische Technik" (Germany) Band 18 1973 No. 5, p. 142.

"IEEE Transactions on Biomedical Engineering" vol. BME-26, No. 7 Jul., 1979, p. 416, A Neonatal Fiberoptic Probe for Oximetry and Dye Curves.

"IEEE Transactions on Biomedical Engineering" vol. BME-23, No. 5, Sep., 1976, p. 391 & Title cover, Multiple Scattering Analysis of Retinal Blood Oximetry.

IEEE Transactions on Biomedical Engineering" vol. BME-25, No. 1 Jan., 1978, p. 28, An Instrument to Measure Cutaneous Blood Flow Using the Doppler Shift of Laser Light.

"IEEE Transactions on Biomedical Engineering", vol. BME-22 No. 3, May, 1975, p. 183 & Title cover, The Choroidal Eye Oximeter: An Instrument for Measuring Oxygen Saturation of Choroidal Blood In Vivo.

"IEEE Transactions on Biomedical Engineering" vol. BME-26 No. 4, Apr., 1979, p. 220, Applications of Photoacoustic Spectroscopy to Problems in Dermatology Research.

The Waters Company Advertisement, received in PTO Oct. 7, 1965 on X-350 Oximeter (Rochester, Minn.).

"Medical & Biological Engineering", vol. 6, 1968 (U.K.), p. 409, Tissue Identification During Needle Puncture by Reflection Spectrometry.

"Medical & Biological Engineering", vol. 10, 1972 (U.K.), p. 385, A Light Emitting Diode Skin Reflectance Oximeter.

"Medical & Biological Engineering & Computing", vol. 18, No. 3, May, 1980, p. 265, Self-stabilising System for Measuring Infrared Light Back-scattered from Vaginal Tissue.

"Medical & Biological Engineering & Computing", Jan., 1980, p. 27 Spectrophotometric monitoring of arterial oxygen saturation in the fingertip.

(List continued on next page.)

U.S. PATENT DOCUMENTS

| | | | |
|---|---|---|---|
| 3,847,483 | 11/1974 | Shaw et al. | 356/41 |
| 3,881,481 | 5/1975 | Heule et al. | 128/2.05 V |
| 3,889,656 | 6/1975 | Krawitt | 128/2 R |
| 3,910,701 | 10/1975 | Henderson et al. | 128/625 |
| 3,958,560 | 5/1976 | March | 128/2.05 E |
| 3,963,019 | 6/1976 | Quandt | 128/2 T |
| 3,980,075 | 9/1976 | Heule | 128/205 T |
| 3,987,303 | 10/1976 | Stoft et al. | 0/343 |
| 3,993,047 | 11/1976 | Peek | 128/2.05 P |
| 4,013,067 | 3/1977 | Kresse et al. | |
| 4,014,321 | 3/1977 | March | 128/2 A |
| 4,015,595 | 4/1977 | Benjamin, Jr. | 128/2.05 V |
| 4,029,085 | 6/1977 | DeWitt et al. | 128/2 R |
| 4,030,485 | 6/1977 | Warner | 128/2 R |
| 4,041,933 | 8/1977 | Reichenberger | 128/2 E |
| 4,048,493 | 9/1977 | Lee | 250/205 |
| 4,063,551 | 12/1977 | Sweeney | |
| 4,073,292 | 2/1978 | Edelman | 128/214 E |
| 4,086,616 | 4/1978 | Catano et al. | 358/81 |
| 4,109,643 | 8/1978 | Bond et al. | 128/2 L |
| 4,109,647 | 8/1978 | Stern et al. | 128/2.05 F |
| 4,114,604 | 9/1978 | Shaw et al. | 128/2 L |
| 4,123,172 | 10/1978 | French | 356/188 |
| 4,157,708 | 6/1979 | Imura | 128/666 |
| 4,163,447 | 8/1979 | Orr | 128/666 |
| 4,166,695 | 9/1979 | Hill et al. | 356/28 |
| 4,167,331 | 9/1979 | Nielsen | 356/39 |
| 4,170,987 | 10/1979 | Anselmo et al. | 128/665 |
| 4,175,545 | 11/1979 | Termanini | 128/666 |
| 4,178,917 | 12/1979 | Shapiro | 128/665 |
| 4,183,360 | 1/1980 | Carlson et al. | 128/666 |
| 4,198,988 | 4/1980 | Cash, Jr. et al. | 128/666 |
| 4,202,339 | 5/1980 | Wirtzfeld et al. | 128/419 PG |
| 4,207,892 | 6/1980 | Binder | 128/665 |
| 4,212,306 | 7/1980 | Mahmud | 128/665 |
| 4,213,462 | 7/1980 | Sato | 128/634 |
| 4,222,389 | 9/1980 | Rubens | 128/633 |
| 4,223,680 | 9/1980 | Jobsis | 128/633 |
| 4,236,526 | 12/1980 | Richard | 128/633 |
| 4,241,738 | 12/1980 | Lubbers et al. | 128/666 |
| 4,249,540 | 2/1981 | Koyama et al. | 128/666 |
| 4,253,447 | 3/1981 | Moore et al. | 128/6 |
| 4,253,744 | 3/1981 | Sawa | 351/16 |
| 4,259,948 | 4/1981 | Urban | 128/6 |
| 4,259,963 | 4/1981 | Huch | 128/635 |
| 4,261,344 | 4/1981 | Moore et al. | 128/6 |
| 4,266,554 | 5/1981 | Hamaguri | 128/633 |

(List continued on next page.)

FOREIGN PATENT DOCUMENTS

| | | | |
|---|---|---|---|
| 54-129786 | 10/1979 | Japan | 128/2 R |
| 124701 | 12/1958 | U.S.S.R. | 128/666 |
| 146905 | 6/1961 | U.S.S.R. | 128/666 |
| 283670 | 8/1971 | U.S.S.R. | 128/634 |
| 311618 | 10/1971 | U.S.S.R. | 128/665 |
| 680725 | 8/1979 | U.S.S.R. | 128/666 |
| 696378 | 11/1979 | U.S.S.R. | 128/666 |
| 704598 | 12/1979 | U.S.S.R. | 128/635 |

(List continued on next page.)

OTHER PUBLICATIONS

"Medical & Biological Engineering & Computing", Mar., 1980, p. 250, Picosecond Laser Stereometry Light Scattering Measurements on Biological Material.

"Medical & Biological Engineering & Computing", vol. 17, No. 3, May, 1979, p. 419, Physiological Light-Emitting Diode Photocell Monitor.

"Medical & Biological Engineering & Computing", vol. 20, No. 1, Jan., 1982, p. 111, Development of an Optical Fibre Technique For He-Ne Laser Screening of Human Body and Its Comparison with the Integrating Sphere Method.

"Analytical Chemistry", vol. 52, No. 6, May, 1980, p. 864, Fiber Optic pH Probe for Physiological Use.

"Medical Instrumentation", vol. 9, No. 3 (May-Jun., 1975), p. 136 Continuous In Vivo Assessment of Arteriovenous Oxygen Difference Utilizing a Fiberoptic Catheter Oximeter.

"Biomedical Engineering & Computing", vol. 5, No. 11 (U.K.), Nov. 1970, p. 549 A New Instrument for Rapid Measurement of Blood Oxygen Saturation and Hb Concentration.

"Medical Instrumentation", vol. 13, No. 4 (Jul.-Aug., 1979), p. 232, A Versatile Simultaneous Multifinger Photocell Plethysmography System for Use in Clinical and Occupational Medicine.

"Biomedical Engineering" (U.S.A.), vol. 12, No. 1, Jan.-Feb., 1978, (published Sep. 1979), p. 20, Instrument for Measuring Microconcentrations of Indicator Dyes in Blood.

"Chest, 76", Jul. 1, 1979, p. 27 Fluorescence Bronchoscopy for Detection of Lung Cancer.

(List continued on next page.)

U.S. PATENT DOCUMENTS

| | | | |
|---|---|---|---|
| 4,267,844 | 5/1981 | Yamanishi | 128/633 |
| 4,281,645 | 8/1981 | Jobsis | 128/633 |
| 4,286,602 | 9/1981 | Guy | 128/665 |
| 4,290,433 | 9/1981 | Alfano | 128/665 |
| 4,295,470 | 10/1981 | Shaw et al. | 128/634 |
| 4,305,398 | 12/1981 | Sawa | 128/633 |
| 4,312,357 | 1/1982 | Andersson et al. | 128/664 |
| 4,321,930 | 3/1982 | Jobsis et al. | 128/633 |
| 4,331,132 | 5/1982 | Mukasa | 128/6 |
| 4,332,258 | 6/1982 | Arai et al. | 128/666 |
| 4,336,809 | 6/1982 | Clark | 128/665 |
| 4,339,954 | 7/1982 | Anson et al. | 73/657 |
| 4,344,438 | 8/1982 | Schultz | 128/634 |
| 4,350,163 | 9/1982 | Ford, Jr. et al. | 128/633 |
| 4,365,307 | 12/1982 | Tatsuwaki et al. | 364/557 |
| 4,366,381 | 12/1982 | Fischer et al. | 250/316.1 |
| 4,370,986 | 2/1983 | Gebhart et al. | 128/716 |
| 4,380,240 | 4/1983 | Jobsis et al. | 128/633 |
| 4,423,736 | 1/1984 | DeWitt et al. | 128/633 |
| 4,446,871 | 1/1984 | Imura | 128/633 |
| 4,467,812 | 8/1984 | Stoller | 128/664 |
| 4,495,949 | 1/1985 | Stoller | 128/664 |
| 4,515,165 | 5/1985 | Carroll | 128/664 |
| 4,541,438 | 9/1985 | Parker et al. | 128/664 |
| 4,570,638 | 2/1986 | Stoddart et al. | 128/665 |
| 4,600,011 | 7/1986 | Watmough | 128/644 |

FOREIGN PATENT DOCUMENTS

| | | | |
|---|---|---|---|
| 786983 | 12/1980 | U.S.S.R. | 128/633 |
| 824995 | 4/1981 | U.S.S.R. | 128/633 |
| 745646 | 2/1956 | United Kingdom | 128/2 A |
| 777651 | 12/1958 | United Kingdom | 356/188 |
| 2068537A | 8/1981 | United Kingdom | 128/665 |
| 2076963A | 12/1981 | United Kingdom | 128/2 L |
| 2092856A | 8/1982 | United Kingdom | 128/366 |

OTHER PUBLICATIONS

"Review of Scientific Instruments", vol. 51, No. 10, Oct., 1980, p. 1403, Endoscopic System for Simultaneous Visual Examination and Electronic Detection of Fluorescence.

"Hewlett-Packard Journal", vol. 28, No. 2, Oct. 1976, p. 2 & Title Cover Sheet Continuous, Non-Invasive Measurements of Arterial Blood Oxygen Levels.

"Laser Electro Optic", No. 1, (1978), U.S.A., p. 22, A Non-Contact High Sensitivity Laser Stethoscope.

"Medicamundi", vol. 17, No. 1 (1972), Abstract & p. 7, The Principle, Design and Features of a New Hb-Oximeter.

"The American Journal of Cardiology", vol. 49, Mar., 1982, p. 743, Simultaneous Measurement of Coronary Venous Blood Flow and Oxygen Saturation During Transient Alterations in Myocardial Oxygen Supply and Demand.

"SPIE", (Soc. Photo-Optical Instrumentation Engineering), vol. 211, (1979), p. 128, Subpicosecond Spectroscopic Techniques in Biological Materials.

"EDN" Sep. 20, 1980, vol. 25, No. 17, p. 69, Fitness and Health-Care Products Incorporate Advanced Electronics.

"Journal of Biomedical Engineering, vol. 4, No. 2, Apr. 1982, p. 142, An Infra-Red Reflectance System for Ambulatory Characterization of Left Ventricular Function.

"IEEE 1979 Frontiers of Engineering in Health Care Conference", Denver, Colo., U.S.A., p. 20, Session 9: Pulse Rate Monitor.

"Vestnik Dermatologi i Venerologii", (Russian), vol. 35, Jun., 1961, pp. 17-20 & 1st sheet of translation The Role of the Luminescence Method in the Diagnosi of Some Dermatoses.

"Proceedings of the 26th Annual Conference on Engineering in Medicine & Biology", Minneapolis, Minn., Sep. 30-Oct. 4, 1973, p. 276, Improved Extracorporeal Reflectance-Oximeter.

"Proceedings of the Thirteenth ISA Aerospace Instrumentation, Symposium", San Diego, Calif., Jun. 13--Jun. 16, 1967, pp. 489 & Title Cover, New Horizons Biomedical Instrumentation.

"IRE" Transactions on Medical Electronics, Jul., 1958, Contents page and Copyright Notice, note p. 34, article on Oximetry by W. Paul.

"IEEE Transactions on Biomedical Engineering", vol. BME-24, No. 2, Mar., 1977, A Proposed Miniature Red/Infrared Oximeter Suitable for Mounting on a Catheter Tip.

"Medical Instrumentation", vol. 7, No. 4, Sep.-Oct., 1973, p. 262, Oxygen Saturation Monitor for Extra-Corporeal Circulation Applications.

"IEEE Transactions on Biomedical Engineering", vol. BME-25, No. 1, Jan., 1978, p. 94, An Electronic Circuit for Red/Infrared Oximeter.

"Medical and Biological Engineering & Computing, Nov., 1979, p. 763, Backscattering of Light by Red Cell Suspensions.

"1979" IEEE International Solid State Circuits Conference, Penna., Feb. 14-16, 1979, p. 202, Session XV: Solid-State Imaging and Biomedical Applications.

ent for optical-response diagnostic apparatus

CROSS-REFERENCE TO RELATED APPLICATION

This application is a continuation-in-part of Applicant's co-pending application Ser. No. 542,022, filed Oct. 14, 1983, now U.S. Pat. No. 4,570,638.

TECHNICAL FIELD

This invention relates generally to optical response apparatus, i.e., apparatus which utilizes light energy as an investigative media and operates by determining the particular response of a given subject to specially-selected and/or specially-applied light energy. More particularly, the invention relates to diagnostic or clinical investigative apparatus which utilizes selected light spectra for assessing the physiological state or condition of biological matter, i.e., tissue, bone, etc., particularly on an in vivo and in situ basis, from the standpoint of transmissivity, or transmissibility, of the subject to the selected light spectra; for example, apparatus such as that disclosed in Applicant's above-identified co-pending application for U.S. patent, now issued as U.S. Pat. No. 4,570,638, which is incorporated herein by reference and of which this application is a continuation-in-part. In a still more particular sense, the present application relates to a testing or examination apparatus, or instrument for utilization in optical response apparatus such as that just referenced, which instrument may generally be considered as being a hand-held and manually-manipulatable device for applying the selected light energy to the subject and collecting the optical-response data resulting therefrom.

BACKGROUND OF THE INVENTION

In Applicant's above-referenced and incorporated co-pending application for U.S. patent, novel apparatus and methodology are disclosed for examining, and appraising the physiological state or condition of biological tissue; in particular, for conducting in vivo examination and assessment of the physiological state of human tissue, for example diagnostic breast (or other) examination of live human subjects.

In accordance with the referenced methodology and apparatus, selected light spectra are introduced into the subject being examined at a first location, and the light energy so infused is then received (e.g., detected) at other particular locations, preferably including both a "near" and "far" such location, for example, near the point of light infusion and generally opposite that point. As described in the referenced co-pending application, the distances between the point of initial light insertion and the points of light reception are important factors in the useful application of the "raw" data (i.e., the particular measured values of the detected light energy). In the referenced application, a vernier-like scale is incorporated in the "optical probe", whereby the particular distance between the two optical "heads" (i.e., the light-producing and the light-receiving instrumentalities) may be determined in any given position to which the two such heads are adjusted to accommodate the size of a particular subject of examination. Such distance determinations, which may be designated "nominal optical distances", were then inputted into the computing apparatus utilized for resolving the data, via the computer control keyboard.

The "optical heads" or components illustrated in the referenced co-pending application basically comprise a light-injection terminal (e.g., the end of a fiber optic bundle or cable), coupled back to a light source (as through the fiber optic cable itself), together with an arrangement of light detector elements, e.g., photovoltaic cells, or photosensors, whose electrical outputs are coupled back to the processing apparatus (e.g., computer) by electrical conductors which extend, with the aforementioned fiber optic cable, from the hand instrument or optical probe to the cabinet which houses a computer, light-generation means, and other apparatus involved. In the embodiment shown in the referenced disclosure, the light-detectors are in effect hooded, being disposed in recessed areas, with optical masks and/or filter elements locatable between the detectors themselves and the subject from which data is to be obtained.

The apparatus in the referenced disclosure, while operative and useful, nonetheless had various features and attributes which were less than completely desirable. For example, the optical probe apparatus was somewhat heavy, as well as somewhat cumbersome; also, the distance-determining means, as noted above, was somewhat rudimentary and susceptible of imprecision, involving the requirement for visual determination together with the need for extra manipulative activity to manually input the data into the computer, both such operations having attendant error-introduction possibilities. Furthermore, as noted above, the referenced apparatus included multiple individual detectors at the optical heads, for multiple data sampling, from different specific locations, permitting extensive analytical processing, through digital computing techniques, and for enhanced accuracy through substantial elimination of spurious or missing data samples.

SUMMARY OF INVENTION

The present invention provides new and improved apparatus and methodology for data-generation test instruments (e.g., optical probes) used in optical-response apparatus of the aforementioned character, in accordance with which system performance and accuracy are improved and operational ease and flexibility are enhanced. Briefly stated, the test instrument in accordance with the invention comprises a lightweight and comparatively inexpensive apparatus which includes new and improved means for controlling and carrying out the optical procedures involved in optical-response examination and analysis of biological tissue and the like, providing highly accurate and repeatable results with substantial ease of operation, at the same time providing for simplified manufacture which affords desirable economy.

In a particular preferred embodiment of the test instrument, first and second optical heads are mounted for movement relative to one another upon an elongated support element, the optical heads being carried by positioning structures extending laterally of the support element. At least one of the optical heads includes a light-emission element, and both such heads preferably carry light-receptors whose output is, ultimately, in electrical form and coupled to signal-processing apparatus, (e.g., a digital computer). The light-receptors preferably comprise light guide elements which receive incident light rays upon their terminal ends and conduct such light to electro-optical detectors, and the light-acceptance angle used for light reception at each of the two optical heads is preferably made uniform, or otherwise coordinated. Such a coordination, or selected relationship, may also be selected for the light-receptors with respect to the light-emission element or elements used. This procedure not only enhances consistency and uniformity in resulting data, but also enables certain selectivity measures which promote accuracy and meaningfulness of data-sampling, providing for increased data contrast and comparison.

Further, the elongated support member of the invention preferably includes "built-in" distance-measuring apparatus which is at least partially housed within the elongated support and operably coupled to the relatively movable optical heads. A signal-transmitting conductor extends from the support element, along with the other electrical conductors and optical cable noted above, back to the control console and the signal-processing apparatus (e.g., computer), such that the nominal optical distance between the two optical heads may be automatically determined and fed to the signal processing apparatus for each and every position of adjustment encountered between the optical heads during normal usage. Additionally, a control switch is preferably incorporated in the test instrument, by which the operator may initiate each test cycle without having to move or change hand positions from the exact position in which the optical heads have been manipulated into optimum placement and adjustment with respect to the test subject.

The advantages provided, and objectives satisfied, by the aforementioned improvements will become more apparent and better understood by reference to the ensuing specification setting forth certain preferred embodiments which illustrate the underlying concept, together with reference to the appended drawings illustrating the such embodiments.

DETAILED DESCRIPTION OF THE PREFERRED EMBODIMENTS

Figure 1:
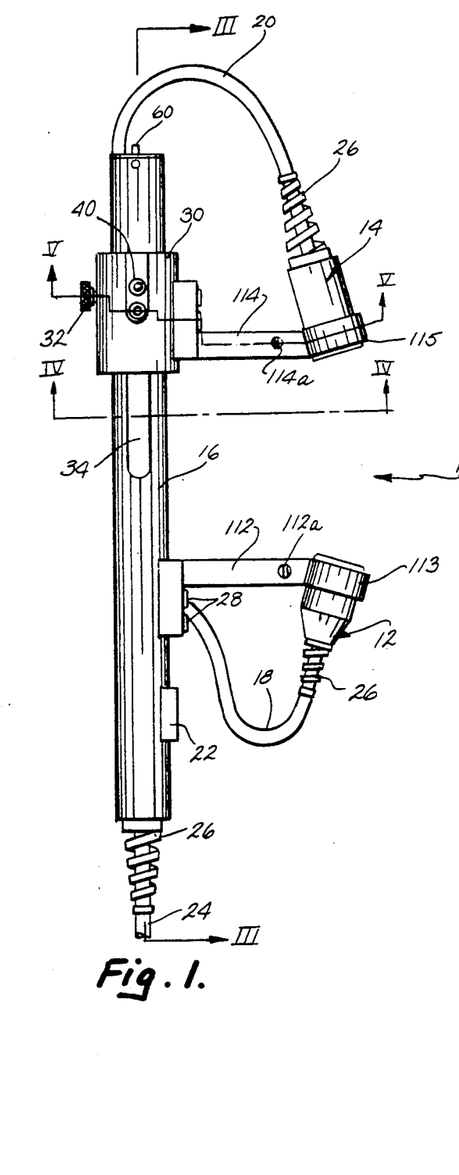
FIG. 1 is a front elevational view of test instrument in accordance with the invention.
Figure 2:
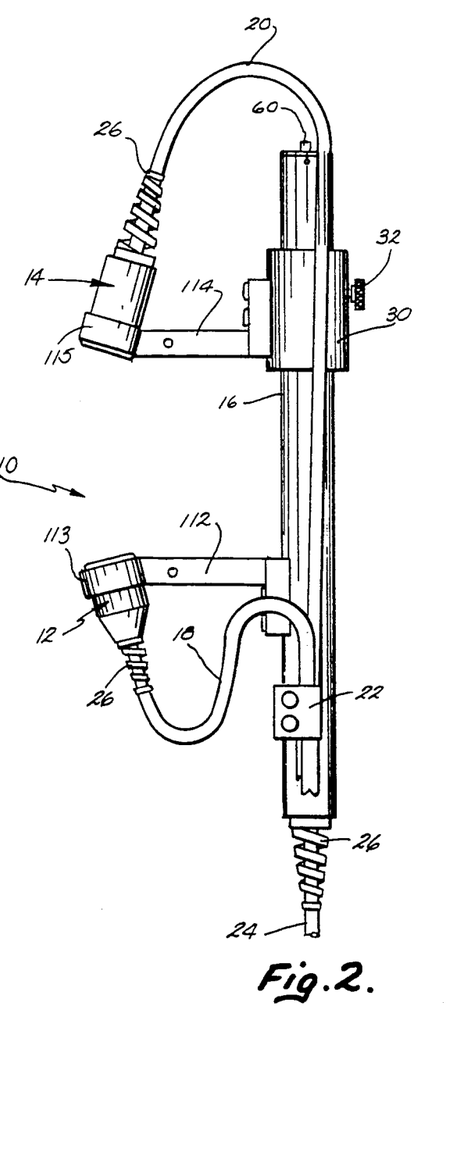
FIG. 2 is a rear elevational view of the apparatus shown in FIG. 1.
Figure 3:
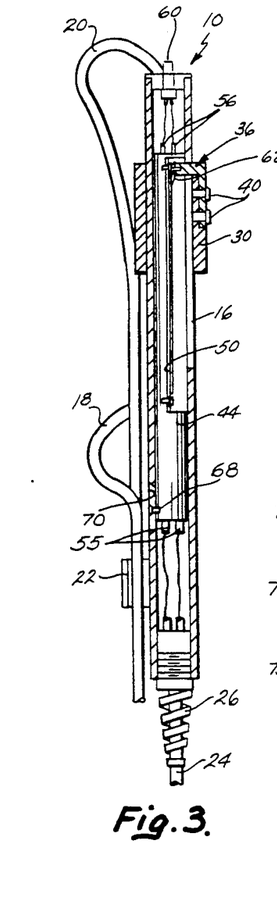
FIG. 3 is a sectional side elevation of the apparatus of FIGS. 1 and 2.

Referring now in more detail to the drawings, the overall nature of the examination instrument or optical probe 10 is best illustrated in FIGS. 1 and 2, from which it may be seen that the same generally comprises first and second optical heads 12 and 14, respectively, mounted upon associated carriers 112, 114, which are in turn mounted upon an elongated support member 16. As illustrated, a cable or conductor 18 extends from the first optical head 12 and a cable or conductor 20 extends from the second optical head 14. Both such cables are preferably routed so as to lie closely along the side of support 16 and are secured in place by a clamp 22 which is attached to support 16 by appropriate screws or the like. Also, a cable or conductor 24 extends outwardly from the lower extremity of support 16, and communicates with the interior thereof. Each of the cables 18, 20, and 24 preferably has suitable strain relief, as by resilient conical spring elements 26, as illustrated.

The optical heads 12 and 14 are movable relative to one another so as to provide for adjustably positioning them on opposite sides of a test subject; for example, the carrier 112 for the first optical head 12 may be fixed in place on support member 16, as by screws 28 or the like, and the carrier 114 which positions the second optical head 14 may be made slidable along the axis of the support 16. To accommodate such relative positioning, cable 20 is preferably unrestrained along its length between clamp 22 and head 14, cable 20 being flexible to accommodate such different positions of adjustment.

In the preferred embodiment illustrated, the elongated support 16 is an essentially rigid tube of generally circular cross section, and carrier 114 is mounted upon a positioning sleeve 30, which has an internal shape complementary to the external shape of support 16 and is slidable therealong. Preferably, sleeve 30 has a manually-actuable position-holding means, or restraint, for example a manual thumbscrew 32 which is threaded through the side of the sleeve and which may be brought to bear against the side of support 16 to hold the adjustment sleeve in place, thus also holding optical head 14 in any given position of adjustment. Optical head 14 is preferably disposed in alignment with optical head 12, the two such heads preferably being in the same general plane. To maintain such positioning, the positioning sleeve 30 is preferably guided in its movement along support 16, as for example by an alignment slot 34, along which a positioning member 36 (FIGS. 3-6, inclusive) moves as the sleeve 30 is slid axially along support 16.

In a particular preferred embodiment, the positioning member 36 comprises an L-shaped structure (FIG. 6) having an elongated mounting tab 38 which fits into an appropriately-sized cooperating slot formed in the side of sleeve 30, where it is held in place by a pair of screws 40 or the like. In this position, a depending guide lug 36a is disposed within a complementary recess cut in the end of sleeve 30, and projects through the positioning slot 34, such that the sleeve 30 may not be rotated with respect to support 16; also, the length of guide slot 34 thus serves to limit the allowable travel of positioning sleeve 30 along support 16, the innermost such position preferably being that in which the optical heads 12 and 14 are positioned closely adjacent one another but not quite in mutual contact.

Inside support 16, an automatic distance-determining apparatus is mounted for cooperation with the movement of positioning sleeve 30 and, as a consequence, the position of optical head 14. In general, this preferably comprises a linear transducer, for example a linear transformer, linear resistor (potentiometer) or optical pick-off, pulse-generator, etc. For example, a ratiometric linear resistor 42 may be used, mounted upon and held in position by an elongated support 44 (FIGS. 3–6, inclusive), which is of semicircular cross section along most of its length but with circular end extremities for automatically achieving accurate positioning inside support 16, to which such circular end extremities are complementary. In this embodiment, potentiometer 42 comprises a pair of generally parallel conductive strips 46 and 48 disposed upon a substrate 50, which is in turn held in place upon the semicircular part of support 44 by flat-headed, countersunk screws 52 or the like. Conductive strips 46, 48 may be energized through appropriate terminals or pin-connectors 54, and the ratiometric output from the potentiometer (or other transducer) appears on another such terminal 55. This signal accurately indicates the distance (separation) between the optical heads, and is coupled back to the control console (and to the signal-processing computer) through a specific conductor comprising part of cable 24. Electrical excitation is also connected through transducer support 44, as by end contacts 56, to an actuation switch 60 which is preferably mounted in the end extremity of the support 16 nearest the adjustment sleeve 30, for reasons explained more fully hereinafter. A particular example of a suitable commercially-available linear transducer is linear resistor model No. MEL-4100-6 sold by Waters Mfg. Inc. of Wayland, Mass. (U.S.A.).

Where a potentiometer such as that described above is used to implement the desired linear (i.e., elongated) transducer, the wiper, or movable contact, for the potentiometer 42 comprises a generally U-shaped element 58 (FIGS. 4, 5 and 6) having an angularly-offset pair of contact legs 62, 64. Wiper 58 is preferably secured in place to the bottom extremity of positioning lug 36a, in the manner generally illustrated in FIGS. 5 and 6, as for example by a pair of tiny screws 66. As will be understood, wiper 58 is an electrically conductive member, and is either insulated from positioning lug 36a or else the latter is made of non-conductive material, e.g., a suitably hard and somewhat lubricious polymeric or filled polymeric, as for example polycarbonate, from which the remainder of the assembly may also be largely constructed, although the support 16 may advantageously comprise a section of aluminum tubing, preferably anodized a dark color (e.g., black). The other components are also preferably opaque and non-reflective, e.g., solid black polycarbonate.

The entire linear transducer assembly, comprising in this embodiment potentiometer 42 and its support 44, are preferably secured in place within the tubular support member 16 by a screw 68 (FIG. 3) which extends through the wall of support tube 16, preferably through an adjustment slot 70 which is elongated in the same direction as the axis of tube 16. Slot 70 is also preferably bevelled along its edges, at an angle complementary to that of the head of counter-sunken screw 68, for a close and substantially flush fit. By such a structure, the position of the linear transducer and its support may be adjusted relative to the length of the support tube, thus providing a zeroing function for calibrating the output of the potentiometer with respect to the relative positioning of the optical heads 12 and 14.

In accordance with the particular embodiment under discussion, the optical head 14 comprises the light-sending component, and optical head 12 comprises a light-receiving component. More particularly, in the preferred embodiment of the overall optical response apparatus, optical head 14 includes both light-sending and light-receiving means, whereas optical head 12 is devoted entirely to light-receiving functions (although these particular attributes could readily be changed, or varied, and head 12 may be used as a light-emission or light-injection source as well).

Figure 4:
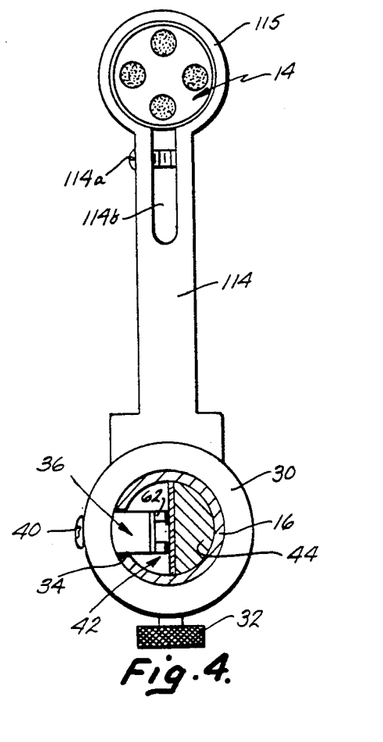
FIG. 4 is a sectional end elevation taken through the plane IV—IV of FIG. 1.
Figure 5:
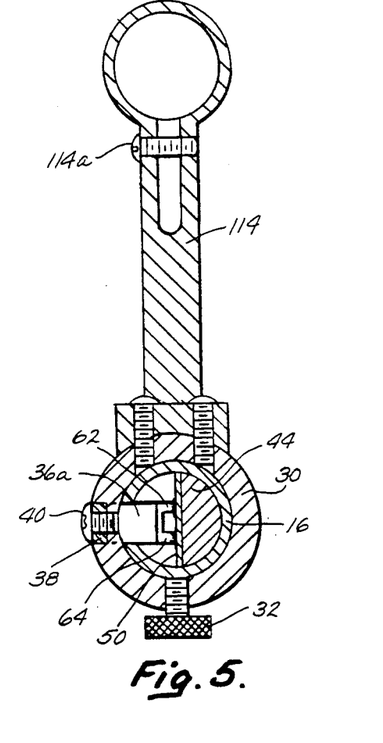
FIG. 5 is a sectional end elevation taken through the plane V—V of FIG. 1.
Figure 6:
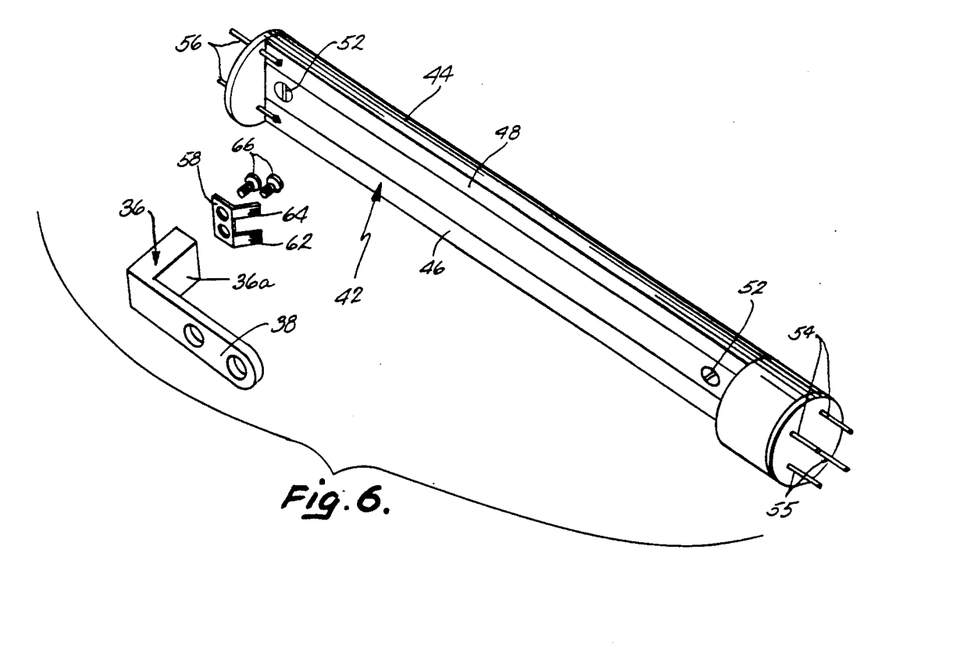
FIG. 6 is an exploded perspective view of the internal distance-measuring apparatus.
Figure 7:
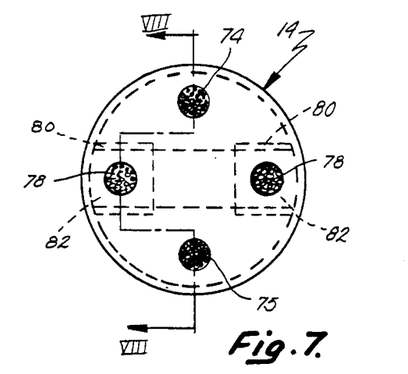
FIG. 7 is an end elevational view of one of the optical heads.
Figure 8:
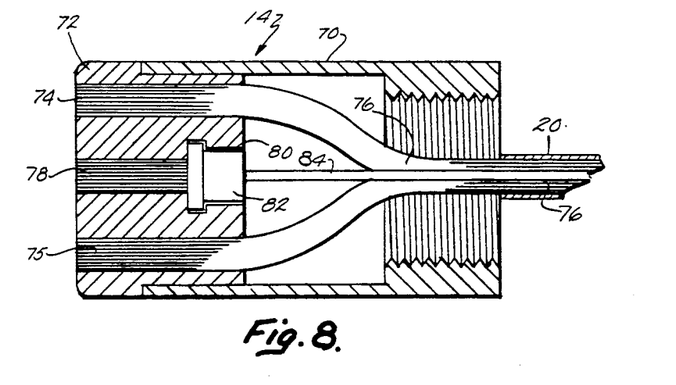
FIG. 8 is a sectional side, elevational view taken through the plane VIII—VIII of FIG. 7.
Figure 9:
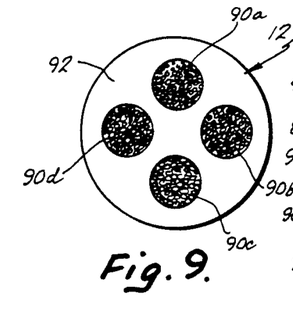
FIG. 9 is an end elevational view of the other optical head.

Thus, with reference to FIGS. 4, 7 and 8, optical head 14 will be seen to comprise an outer housing 70 which is mechanically connected to an opaque terminal block or end piece 72 of generally cylindrical form. Optical head 14 is mounted in place within its carrier 114 by a mounting ring 115 (FIG. 4) which may be contracted about the outside of housing 70 by a screw 114a passing through a slot 114b in carrier 114.

The terminal block or end piece 72 of head 14 includes four equally-spaced passages, two of which receive the bifurcated ends 74, 75 of a fiber optic cable or bundle 76, through which the incident light is applied to the subject. In this regard, the two-position double light source configuration shown is preferred, although not essential, for improved system operation since it helps to infuse light into a selected sample location in a more selective yet more thorough manner, thus enhancing uniformity of resulting data. The other two passages in end piece 72 receive comparatively short light guides 78, which are preferably short sections of optical fiber bundle of the same type as used in cable 76. Light guides 78 extend inwardly of the terminal block 72 to communicate with a pair of oppositely-spaced recesses 80, in each of which are mounted an electro-optical light-detector 82 whose external shape is preferably generally complementary to that of such recesses. Thus, light rays impinging upon optical head 14 are incident upon the outward end extremities of light guides 78 (which may be referred to as "optically active" terminals, or terminations), and such light is transmitted by these light guides to the detectors 82. As indicated above, such detectors are electro-optical elements (e.g., photosensors, etc.), which have electrical outputs; thus, they are coupled to input and output electrical conductors 84. These conductors, with the fiber optic bundle 76, exit optical head 14 as the aforementioned cable 20. Preferably, detectors 82 mount within terminal block 72 through complementary-shaped and appropriately-sized recesses 80 formed through the two opposite sides of the terminal block. Such recesses may be closed by appropriate press-fit plugs (not shown) which help retain the detectors in place, although the basic position of the detectors is determined by their complementary symmetry with recesses 80.

Figure 10:
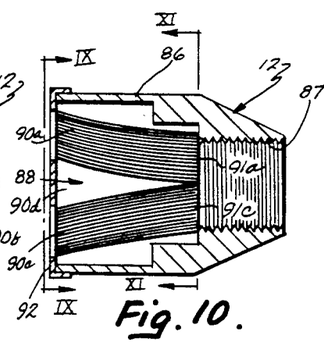
FIG. 10 is a sectional side elevational view taken through the plane X—X of FIG. 9.
Figure 11:
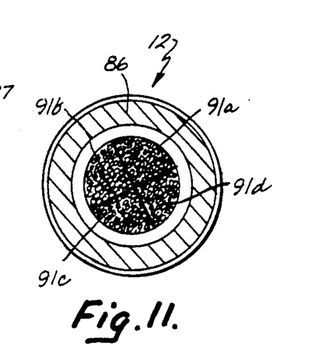
FIG. 11 is a rear end elevational view of the apparatus of FIG. 10, as seen from the plane XI—XI of FIG. 10.

Optical head 12 mounts within an encircling ring 113 provided by its carrier 112, in the same general manner as optical head 14, discussed above, but is of different construction. Optical head 14 includes an outer housing or ferrule 86 (FIG. 10) inside which is disposed, in accordance with the particular preferred embodiment illustrated, a four-sided fiber optic or other optically-conductive light-receptor member 88. In this particular preferred embodiment, light-receptor 88 has four divergent cylindrical end portions 90a, 90b, 90c and 90d of circular cross section which are positioned by an apertured end mask 92 in the form of a cap which fits over the end extremity of ferrule 86. At the opposite end of light-receptor member 88, the four optical conductors are formed into mutually-interfitting generally triangular quadrants 91a, 91b, 91c and 91d, respectively, whose collective outer perimeter defines a generally circular shape. This configuration allows for parallel reception of the light energy received at each of the mutually-spaced, and thus differently-positioned, light-reception locations represented by the fiber optic bundle terminations 90a, 90b, 90c and 90d which face optical head 14. Accordingly, specifically different areas of the subject may be sampled, and the resulting light-reception data may be summed, to provide an integration function which is useful for such purposes as averaging-out local data abberations, accumulating higher total levels of detected resultant light from the subject, etc. Of course, this particular embodiment is basically an enhancement or extension of the simplest version of a preferred receptor in accordance herewith (i.e., a single light guide and matched electro-optical detector) and need not be utilized in all cases if not desired. Further, the concept may be implemented in varying ways as by changing the spacing between and/or particular positioning of the optically-active cable terminations 90a-90d, as well as by single-ending the opposite ends 91a-91d, i.e., keeping the optical response data from these elements separate from one another rather than paralleling them, to maintain different discrete sample points.

In accordance with the preferred embodiment illustrated, the closely-adjacent, paralleled, optical cable or light guide terminations 91a, 91b, 91c and 91d may all be monitored by a single receptor, disposed within the internally-threaded aperture 87 shown in the rear of housing or ferrule 86. Such a unitary receptor may comprise a single, composite fiber optic bundle termination, in which case the cable 18 exiting optical head 12 would comprise a fiber optic cable. A more preferred arrangement is to utilize a single electro-optical detector (e.g. photodetector or photovoltaic cell) secured within aperture 87 and optically indexed to the terminations 91a, 91b, 91c and 91d, which are thus coupled in parallel (as would of course also be the case if a common fiber optic bundle was indexed to these adjacent terminations). Where the preferred electro-optical detector is used at the ends 91a-91d, the cable 18 exiting optical head 12 comprises only electrical conductors. In the case of both optical head 12 and head 14, the use of electro-optical detectors located within the heads themselves, and the resultant presence of small and light-weight electrical conductors as all or part of cables 18 and 20, provides a significant and desirable reduction in weight and bulk, augmenting and enhancing the operation of the instrument due to the reduced weight, increased flexibility of the attaching cables, etc. In this regard, the optical fiber bundle 76 communicating with head 14 could, at least conceivably, be replaced by electrical wiring also, with actual light-generation means (i.e., lamps, etc.), mounted within head 14; however, the arrangement illustrated and described above is presently deemed more preferred, and the presence of a single fiber optic bundle within cable 20 does not represent a significant obstacle in terms of bulk, inflexibility, etc.

The preferred arrangement and structure described above with respect to the terminal block 72, and in particular with regard to the light guides 78 and detectors 82, is much more than a mere matter of accommodation. On the contrary, the concept underlying this structure and arrangement is of considerable importance to the most effective functioning of the overall optical response diagnostic apparatus comprising the most preferred usage for the instrument disclosed herein. More particularly, the aperture number, or acceptance angle, of most electro-optical detectors is considerably different than that of a fiber optic cable termination or light guide end extremity; also, the effective acceptance angle of the light-guided detector arrangement shown is considerably different from other possible optical arrangements such as hooded or recessed mounting of the detectors, etc. That is, by utilizing a light guide 78 of a similar nature to, or otherwise selectively correlated with, the terminations 74 and 75 of input optical cable 76, and by matching the detector 82 to the inward termination of light guide 78, a particular optical correlation is obtained between the light-infusion characteristics at the optical cable terminations 74 and 75, where light enters the subject being examined, and the receptors 78, represented by the optical fiber bundle terminations described.

Optical correlation as noted in the above discussion of optical receptor 78, is also preferably established between receptor 78 and each of the mutually-spaced and differently-positioned light-receptor points at optical head 12, represented by the optical disposition (structure and positioning) of cable terminations 90a-90d, inclusive. This correlated optical disposition provides more than mere uniformity per se, however, as desirable as that condition may be; more particularly, the arrangement provides for a more limited acceptance angle than would be true of detectors (or for that matter light source elements) located directly adjacent the skin or other boundary of the subject being examined, in which case the acceptance angle would be very wide, approaching one hundred eighty degrees. Optical cable terminations act much more restrictively, and in effect comprise, sampling restrictors, since their acceptance angle may be on the order of, for example, only sixty degrees, thus allowing entry of only those light rays which are more directly oriented at the receptor point, including some rays of acutely angular incidence but excluding those which are incident at a comparatively wide angle. This provides for more concise and more particularly-defined sampling activity, and it is to be noted that the preferred methodology discussed in the above-referenced, and incorporated, prior application now issued as U.S. Pat. No. 4,570,638 includes the concept of examination at at least a small number of separate and specifically-located positions on the test subject (for example, in human breast examination, data is taken at four mutually-spaced locations on each breast). It has been found that the desirable results of this technique are to some extent impaired or obscured by increasingly wide-angle reception of the light which has been infused into the test subject, and this result is deemed disadvantageous from the standpoint that, as taught in the referenced application just identified, a significant part of the advantageous interpretation of the resulting conditioned data involves contrast comparisons between the data received at comparable locations on physiologically paired test subjects, e.g., opposite breasts of the same subject, and/or contrasting comparison of data from a particular location on one test subject to comparable data obtained from the same defined location in a large data base representing the norm or average for that particular location. Thus, while it is possible that the wide-angle reception technique just noted provides other and desirable benefits under different interpretative methodologies, the more selective technique described with respect to optical heads 12 and 14 herein, as illustrated for example in FIGS. 8 and 10, certainly has specific and desirable benefits and advantages in and of itself.

It will be noted that the optical heads 12 and 14 are preferably disposed at a small, acute angle with respect to the axis of their corresponding carriers 112 and 114, i.e., the respective mounting rings 113 and 115 (FIGS. 1 and 2) being offset from each carrier axis accordingly. This arrangement is different from that disclosed in the above-referenced and incorporated co-pending application (now U.S. Pat. No. 4,570,638), and has been found to be particularly advantageous in the use of the instrument 10 for in vivo breast examination. That is, in typical human physiology the breast is of a generally conical nature, having a certain taper, and the preferred modality in using the instrument 10 is to place the breast between optical heads 12 and 14 at each of the different predetermined test locations and then to move head 14 toward head 12 and into a position where both of the heads are in firm (but not overly tight) contact with the skin. Of course, due to the inherent softness of the breast structure, the heads 12 and 14 will typically become embedded at least slightly, but it is desired to obtain firm contact between the skin and the optical components across the entire area of the optical heads without any discomfort to the test subject. Consequently, due to the conical shape of the human breast, the acute angle illustrated is a desirable and advantageous feature, allowing the entire surface of each head to be lightly embedded into the breast in a comparatively uniform manner, without undue differences in pressure.

The presence of the actuation switch 60 (FIGS. 1, 2 and 3) on the examination instrument 10, and indeed in close proximity to the movable adjustment sleeve 30, is also a distinctly advantageous feature. That is, in the successful operation of the apparatus, it is typically desirable to have both of the optical heads 12 and 14 in light but firm contact with the subject or material being examined and, particularly in the case of human breast examination, it is important to the consistent and accurate performance of the instrument as well as to the comfort of the patient that the appropriate positioning of the instrument vis-a-vis the breast being examined become established and consistently maintained throughout the brief test procedure during which light is infused into the breast and detected at both of the optical heads.

Accordingly, while it is definitely of advantage to have a locking mechanism for securing the adjustment sleeve 30 in the desired position which properly locates optical heads 12 and 14 for each different patient or examination subject, it is also very advantageous to have the test-actuation switch immediately at hand, preferably in a location where the hand of the operator is already in position to actuate such switch when the instrument 12 has been placed in the desired position and the sleeve 30 brought to its desired location. It will be appreciated that by locating the switch 60 in the position shown, this objective is very advantageously achieved, switch 60 being wired back to the control console, as for example by conductors extending through the potentiometer support 44, such that actuation of switch 60 opens or closes a path for current flow and thus serves to provide a logic signal to the control console when the switch is actuated. Thus, the occurrence of this signal may be used to initiate the optical-response examination sequence, involving the emission of selected light spectra from optical terminations 74 and 75 for infusion into the examination subject, ensuing sampling of light by the receptors, etc. Of course, the positioning of the adjustment sleeve 30 and optical head 14 establishes the corresponding position of the wiper arms 62 and 64 along their corresponding conductive strips 46 and 48; consequently, the output signal provided by transducer 42 (whether or not switch 60 is connected to, or through, the latter) is a direct indication of the relative positions of optical heads 12 and 14, i.e., an automatic and accurate measurement of the distance therebetween. Once again, the effective zero position of the potentiometer, indicating zero distance between optical heads 12 and 14, may be adjusted by use of the securement screw 68 shown in FIG. 3, by which the potentiometer may be moved with respect to its wiper arms (and with respect to sleeve 30), and then secured firmly in place to provide a zero reading at the desired position of head adjustment.

It is to be understood that the above detailed description is that of one exemplary preferred embodiment of the invention, and that numerous changes, alterations and variations may be made without departing from the underlying concepts and broader aspects of the invention as set forth in the appended claims, which are to be interpreted in accordance with the established principles of patent law, including the doctrine of equivalents.

The embodiments of the invention in which an exclusive property or privilege is claimed are identified as follows:

1. An examination instrument for use with optical response apparatus, comprising in combination:
    means defining a main support structure; first and second optical heads, and means for mounting said heads upon said support structure for movement relative to one another; at least one of said optical heads including light-emission means for applying light energy to a test subject, and at least the other of said optical heads including light-receptor means for receiving light applied to the test subject by said emission means; conductor means for operatively connecting said first and second optical heads to light source excitation and light reception data-processing apparatus, respectively; and means for outputting a variable signal having values which are individually representative of particular distances between said optical heads at different positions of relative movement therebetween, said means including signal-conveying means extending from at least one of said support structure and said optical heads for conveying said variable signal to signal-processing apparatus.

2. The examination instrument according to claim 1, wherein said means for outputting representative signals comprises an electrical device and said signals are electrical signals.

3. The examination instrument according to claim 2, wherein said electrical device comprises a linear transducer.

4. The examination instrument according to claim 1, wherein at least one of said optical heads is movable, and including means for coupling said at least one of said optical heads to said means for outputting representative signals, whereby changes in said output signals correspond to movement of said one optical head.

5. The examination instrument according to claim 1, wherein said support structure includes means defining a substantially enclosed internal recess, and wherein said means for outputting representative signals is located at least partially within said recess.

6. The examination instrument according to claim 5, and including means for coupling at least one of said optical heads to said means for outputting representative signals such that said relative movement of said optical heads produces corresponding change in said signal-outputting means.

7. The examination instrument according to claim 5, wherein said means for outputting representative signals comprises an electrical component substantially enclosed within said internal recess.

8. The examination instrument according to claim 7, wherein said component comprises a potentiometer having a movable contact, and including means for coupling said movable contact to at least one of said optical heads such that said relative movement of said optical heads moves said contact to produce corresponding changes in said signals.

9. The examination instrument according to claim 8, wherein said means for mounting said heads upon said support structure for movement includes a positioning member slidably interfitted with portions of said support structure, and wherein said slidable positioning member is coupled to said movable contact to impart movement thereto corresponding to sliding movement of said positioning member with respect to said support structure.

10. The examination instrument according to claim 9, wherein said support structure comprises a generally tubular member generally enclosing said potentiometer, said member having an axially-extending side opening; and an arm connected to said positioning member and extending through said opening, said arm being coupled to said movable contact to move the same as said positioning member is moved.

11. The examination instrument according to claim 10, wherein said side opening comprises a guide slot and said connecting arm which extends through said opening comprises a guide lug movable along said slot, said guide slot and lug at least partially guiding the movement of said positioning member.

12. The examination instrument according to claim 1, wherein said support structure comprises an elongated member, wherein said means for mounting said heads upon said support structure comprise stand-off members which hold said heads a predetermined distance alongside said elongated member, and wherein said stand-off members include means for mounting at least one of said optical heads at an angle with respect to the longitudinal axis of said elongated member.

13. The examination instrument according to claim 12, and including means for mounting both of said optical heads at an acute angle with respect to the said axis of said elongated support member.

14. The examination instrument according to claim 13, wherein said means for mounting said optical heads position the two such heads at oppositely-disposed acute angles with respect to said axis and to one another, so as to accommodate an oppositely-tapered examination subject between said heads.

15. An examination instrument for use with optical response apparatus, comprising in combination:
an elongated support member; first and second optical heads, and means for mounting said heads upon said support member for movement relative to one another; at least one of said optical heads including light-emission means for applying light energy to a test subject, and at least the other of said optical heads including light-receptor means for receiving light applied to the test subject by said emission means; conductor means for operatively connecting said first and second optical heads to light source excitation and light-reception data-processing apparatus, respectively; said means for mounting said optical heads upon said support member comprising stand-off elements which hold said heads a predetermined distance alongside said support member; and means associated with said stand-off elements for mounting at least one of said optical heads upon its corresponding stand-off element at an angle with respect to the longitudinal axis of said elongated support member.

16. The examination instrument according to claim 15, wherein said means for mounting said optical heads position the two such heads at oppositely-disposed acute angles with respect to said axis and to one another, so as to accommodate an oppositely-tapered examination subject between said heads.

17. An examination instrument for use with optical response apparatus, comprising in combination:
means defining a hand-held support member; first and second optical heads, and means for mounting said heads upon said support member for movement of one such head relative to the other; at least one of said optical heads including light-emission means for applying light energy to a test subject, and at least the other of said optical heads including light-receptor means for receiving light applied to the test subject by said emission means; conductor means for operatively connecting said first and second optical heads to light source excitation and light-reception data-processing apparatus, respectively; and control switch means carried with said support member, for providing a control signal to said data-processing apparatus to designate the desired commencement of data-processing operations by said apparatus.

18. The examination instrument according to claim 17, wherein said control switch means comprises an electrical device and said control signal is an electrical signal.

19. The examination instrument according to claim 18, wherein said electrical device comprises a switch mounted upon at least one of said support member and said optical heads.

20. The examination instrument according to claim 19, wherein said switch is mounted upon said support member in proximity to one of said optical heads.

21. The examination instrument according to claim 20, wherein at least one of said optical heads is movably mounted upon said support member and said electrical switch is mounted in close proximity to said movably-mounted head.

22. The examination instrument according to claim 17, and including means carried by said hand-held support member for outputting a variable signal having values which are individually representative of the particular distance between said optical heads at different positions of relative movement therebetween, said means including signal-conveying means extending from at least one of said support member and said optical heads for conveying said variable signal to signal-processing apparatus.

23. The examination instrument according to claim 22, and including means for mounting said optical heads upon said support member, said means comprising stand-off elements which hold said heads a predetermined distance alongside said support member; and means associated with said stand-off elements for mounting at least one of said optical heads upon its corresponding stand-off element at an angle with respect to the longitudinal axis of said support member.

24. An examination instrument for use with optical response apparatus, comprising in combination:
first and second optical heads, a support structure, and means for mounting said heads upon said support structure for movement relative to one another; at least one of said optical heads including light-emission means for applying light energy to a test subject, and at least the other of said optical heads including light-receptor means for receiving light applied to the test subject by said emission means; and said light-receptor means of at least said other optical head comprising a light-conductive member having an optically-active termination arranged to receive light from said test subject and to convey such light away from said subject through such light-conductive member.

25. An examination instrument according to claim 24 wherein said support structure comprises an elongated member, and including means for mounting said optical heads upon said support member, said means comprising stand-off elements which hold said heads a predetermined distance alongside said support member; and means associated with said stand-off elements for mounting at least one of said optical heads upon its corresponding stand-off element at an angle with respect to the longitudinal axis of said support member.

26. The examination instrument according to claim 25, wherein said light-emission means of said at least one optical head comprises a light-conductive member having an optically-active termination arranged to emit light conducted by such member to a test subject.

27. The examination instrument according to claim 26, and including means for positioning both of said light-conductive members at their corresponding optical heads such that both of said active terminations of said light-conductive members are brought into contact with said test subject when their corresponding optical heads are brought into optical engagement with such test subject.

28. The examination instrument according to claim 24, wherein said light-receptor means of at least said other of said optical heads includes an electro-optical light detector and means mounting said detector and the said light-conductive member of said other head in optical communication with one another such that light received by said optically-active termination is applied to said detector at said other optical head.

29. The examination instrument according to claim 28, wherein both of said optical heads include at least one of said light-receptor means comprising an electro-optical detector mounted for cooperative light communication with a light-conductive member of the respective optical head.

30. The examination instrument according to claim 29, wherein at least one of said optical heads includes a terminal structure for mounting the light-conductive member and detector of that optical head, said terminal structure defining recesses for receiving said optically-conductive member and said detector and for maintaining same in mutual optical communication.

31. The examination instrument according to claim 26, wherein said one optical head which includes said light-emission means comprising a light-conductive member further includes a light receptor comprising an electro-optical light detector device and a light-conductive member disposed to receive incident light at said one optical head and to convey such light to said detector device.

32. The examination instrument according to claim 24, wherein said one optical head which includes said light-emission means further includes a light receptor comprising at least in part a light-conductive member.

33. The examination instrument according to claim 32, wherein said light-conductive member of said one optical head has an optically-active termination arranged to receive light from said test subject and to convey such light away from said subject through said different light-conductive member.

34. The examination instrument according to claim 33, wherein said light receptor of said one optical head further comprises an electro-optical light-detector device, said device being disposed in light communication with said light-conductive member to receive input light therefrom.

35. The examination instrument according to claim 24, wherein said light-conductive member of said light-receptor means at said other optical head comprises at least two mutually-spaced light-guide portions.

36. The examination instrument according to claim 35, wherein said mutually-spaced light-guide portions have separate optically-active light-receiving terminations which are spaced apart from one another.

37. The examination instrument according to claim 36, wherein said mutually-spaced light-guide portions are optically paralleled at a point spaced from said light-receiving terminations.

38. The examination instrument according to claim 37, and including an electro-optical light-detector device arranged in optical communication with said optically-paralleled light-guide portions to receive light conducted by any of such portions.

39. The examination instrument according to claim 32, wherein said light-emission means of said one optical head comprises a light-conductive member different from the light-conductive member of said light receptor at said one head, and wherein said light-conductive member of said light receptor has an optically-active termination arranged to receive light from said test subject and to convey such light away from said subject through such light-conductive member.

40. The examination instrument according to claim 39, wherein said light receptor of said one optical head further comprises an electro-optical light-detector device, said device being disposed in light communication with said light-conductive member to receive input light therefrom.

41. The examination instrument according to claim 40, and including an electro-optical light-detector device arranged in optical communication with said light-conductive member of said other optical head, whereby such light-detector device receives light through said communicating light-conductive member from its said optically-active terminations.

42. The examination instrument according to claim 41, wherein all of said optically-active terminations are mounted in optically correlated disposition with one another so as to access the subject under examination with correlated light-acceptance angles.

43. The examination instrument according to claim 42, wherein all of said optically-active terminations are mounted in substantially the same optical disposition with one another so as to access the subject under examination with substantially the same optical acceptance angles.

44. The examination instrument according to claim 26, wherein the light-conductive member of at least said one optical head includes at least two light-emission elements and said elements are mutually spaced over at least portions of their extremities.

45. The examination instrument according to claim 44, wherein said two mutually-spaced portions of said light-emission elements comprise parallel-connected light-guide elements.

46. The examination instrument according to claim 45, wherein said two mutually-spaced portions of said light-emission elements are disposed generally diametrically opposite one another with respect to the optically-active face of said at least one optical head.

47. The examination instrument according to claim 45, wherein said two mutually-spaced portions of said light-emission elements comprise bifurcated portions of a common light-conductive optical cable.

48. In a method of optically examining biological-type material to assess its physiological or conditional state, wherein light energy is infused into said material at at least a first location with respect thereto and resultant light energy is detected at at least one other location on the material, the improvement comprising the steps of:
infusing said light energy into said material by applying light externally thereto at at least said first location from a light source having a predetermined angle of light emission, and detecting the resulting light energy infused into said subject by optically accessing the material at at least said other location with light-receptor means having an optical acceptance angle particularly correlated to said predetermined angle of light emission.

49. The improvement for an optical examination method as set forth in claim 48, wherein said predetermined angle of light emission and said optical acceptance angle are of substantially the same effective value.

50. The improvement for an optical examination method as set forth in claim 48, wherein said predetermined angle of light emission and said optical acceptance angle are selected to have a restricted effective value.

51. In a method of optically examining a subject comprising biological or other such material to assess its physiological or conditional state, wherein light energy is applied to said subject at at least a first location with respect thereto and resultant infused light energy is detected at at least two mutually-separated locations on the subject, the improvement comprising the steps of detecting the resulting light energy infused into said subject by optically accessing the subject at each of said at least two mutually-separated locations using light receptors having optical acceptance angles which are particularly correlated to one another.

52. The improvement for an optical examination method as set forth in claim 51, wherein said optical acceptance angles used to access the subject at said at least two mutually-separated locations are of substantially the same effective value.

53. The improvement for an optical examination method as set forth in claim 51, wherein said optical acceptance angles used to access the subject at said at least two mutually-separated locations are selected to have a restricted effective value.

54. The improvement for an optical examination method as set forth in claim 51, including the steps of applying said light energy to said subject at a predetermined angle of incidence, and selecting said predetermined angle of incidence to have an effective value which is correlated with said optical acceptance angles used in detecting the resulting light energy at said at least two mutually-separated locations.

55. The improvement for an optical examination method as set forth in claim 54, wherein said predetermined angle of incidence and said optical acceptance angle are selected to have a restricted effective value.

56. An examination instrument for use with optical response apparatus, comprising in combination:
means defining a support member; first and second optical heads, and means for mounting said heads upon said support member for movement of one such head relative to the other; at least one of said optical heads including light-emission means for applying light energy to a test subject, and at least the other of said optical heads including light-receptor means for receiving light applied to the test subject by said emission means; control means in close proximity to at least said one movable head, for providing a signal to designate the desired commencement of optical-response operations by said optical-response apparatus;
means operatively coupled to at least said one movable head for outputting a variable signal having values which are individually representative of the particular distance between said optical heads at different positions of relative movement therebetween;
means for mounting said optical heads upon said support member, said means comprising stand-off elements which hold said heads a predetermined distance from said support member; means associated with said stand-off elements for mounting at least one of said optical heads upon its corresponding stand-off element at an acute angle with respect to the longitudinal axis of such stand-off element;
said light-emission means of said at least one optical head comprising a light-conductive member having an optically-active termination arranged to emit light conducted by such member to a test subject; and said light-receptor means of at least said other optical head comprising a light-conductive member having an optically-active termination arranged to receive light from said test subject and to convey such light away from said subject through such light-conductive member; said one optical head which includes said light-emission means further including a light receptor comprising an electro-optical light-detector device and a light-conductive member having an optically-active termination disposed to receive light from said test subject at said one optical head for said light-conductive member to convey to said detector;
all of said optically-active terminations having optical characteristics which are particularly correlated with one another so as to access the subject under examination with correlated optical acceptance angles.

* * * * *